US005681565A

United States Patent [19]
Gristina et al.

[11] Patent Number: 5,681,565
[45] Date of Patent: *Oct. 28, 1997

[54] METHODS AND COMPOSITIONS FOR PASSIVE IMMUNOTHERAPY

[75] Inventors: Anthony G. Gristina, Reston; Girish Giridhar, Manassas Park, both of Va.

[73] Assignee: Medical Sciences Research Institute, Herndon, Va.

[*] Notice: The term of this patent shall not extend beyond the expiration date of Pat. No. 5,505,945.

[21] Appl. No.: 590,880

[22] Filed: Jan. 24, 1996

Related U.S. Application Data

[63] Continuation-in-part of Ser. No. 295,482, Aug. 25, 1994, Pat. No. 5,505,945, which is a continuation of Ser. No. 3,305, Jan. 12, 1993, abandoned.

[51] Int. Cl.$^6$ .................. A61K 39/40; A61K 39/085; A61K 39/09; A61K 39/104
[52] U.S. Cl. .................. 424/164.1; 424/130.1; 424/141.1; 424/150.1; 424/163.1; 424/165.1; 424/169.1; 424/170.1; 530/387.1; 530/388.1; 530/388.2; 530/388.4; 530/389.1; 530/389.5
[58] Field of Search .................. 424/164.1, 130.1, 424/141.1, 150.1, 163.1, 165.1, 169.1, 170.1; 530/387.1, 388.1, 388.2, 388.4, 389.1, 389.5

[56] References Cited

PUBLICATIONS

Gristina, "Biomaterial–Centered Infection: Microbial Adhesion Versus Tissue Integration", Science, vol. 237, 25 Sep. 1987, pp. 1588–1595.
Gristina et al., "Biomaterial–Centered Sepsis and the Total Artificial Heart", Journal of the American Medical Association (JAMA), vol. 259, Feb. 12, 1988, pp. 870–874.
Gristina et al., "Molecular Mechanisms in Musculoskeletal Sepsis: The Race for the Surface", Instructional Course Lectures, vol. XXXIX 1990, American Academy of Orthopaedic Surgeons, pp. 471–482.
Buckley et al., "The Use of Intravenous Immune Globulin in Immunodeficiency Diseases", New England Journal of Medicine, Jul. 11, 1991, pp. 110–117.
Cometta et al., "Prophylactic Intravenous Administration of Standard Immune Globulin . . . ", New England Journal of Medicine, vol. 327, No. 4, Jul. 23, 1992, pp. 234–239.
Siber et al.,"Use of Immune Globulins in the Prevention and Treatment of Infections", Current Clinical Topics in Infectious Diseases, vol. 12 pp. 208–256.
Panlilio et al.,"Methicillin–Resistant *Staphylococcus aureus* in U.S. Hospitals, 1975–1991", Infection Control and Hospital Epidemiology, vol. 13, No. 10, Oct. 1992, pp. 582–586.
Emori et al., "Nosocomial Infections in Elderly Patients in the United States, 1986–1990", American Journal of Medicine, vol. 91(suppl 3B), pp. 3B–289S–293S.
Siber, "Immune Globulin to Prevent Nosocomial Infections", New England Journal of Medicine, vol. 327, No. 4, pp. 269–271.

Ma, "Prevention of Colonization of Streptococcus Mutans by Topical Application of Monoclonal Antibodies . . . ", Arch Oral Biol 1990; 35 Suppl;115S–122S(abstract).
Gristina, "Materials, Microbes and Man: the Problem of Infection Associated With Implantable Devices", Current Perspectives on Implantable Devices, vol. 1, JAI Press Inc., pp. 71–137.
Gristina, "Biomaterial Specificity, Molecular Mechanisms and Clinical Relevance of *S. epidermidis* and *S. aureus* Infections in Surgery", Zbl. Bakt. Suppl. 16, Gustav Fischer Verlag, 1987.
Kojima, "Antibody to the Capsular Polysaccharide/Adhesion Protects Rabbits . . . ", Journal of Infectious Diseases 1990;162, Aug., pp. 435–441.
Mandell (ed.), *Principles and Practice of Infectious Diseases*, 2nd Ed., John Wiley and Sons, 19—?, Chapter 5, pp. 37–43.
Behre et al., "Endotoxin Concentration in Neutropenic Patients with Suspected Gram–Negative Sepsis", Antimicrobial Agents and Chemotherapy, vol. 36, No. 10, Oct. 1992, pp. 2139–2146.
van Furth et al., "Correlation Between Opsonic Activity for Various Microorganisms and Composition of Gammaglobulin Preparations for Intravenous Use", Journal of Infectious Diseases, Vo. 149, No. 4, Apr. 1984, pp. 511–517.
Givner et al., "A Polyclonal Human IgG Preparation Hyperimmune for Type III, Group B Streptococcus", Journal of Infectious Diseases, vol. 158, No. 4, Oct. 1988, pp. 724–728.
Emori et al., "National Nosocomial Infections Surveillance System (NNIS) . . . ", American Journal of Infection Control, vol. 19, No. 1, Feb. 1991, pp. 19–35.
Culver et al., "Surgical Wound Infection Rates by Wound Class, Operative Procedure, and Patient Risk Index", American Journal of Medicine, vol. 91(Suppl 3B), Sep. 16, 1991, pp. 3B–152–S–3B–157S.
"Nosocomial Infection Rates for Interhospital Comparison . . . ", Infection Control and Hospital Epidemiology, vol. 12, No. 10, pp. 609–621.
Jarvis et al., "Nosocomial Infection Rates in Adult and Pediatric Intensive Care Units in the United States", American Journal of Medicine, vol. 91(Supp3B) Sep. 16, 1991 pp. 185S–191S.

(List continued on next page.)

*Primary Examiner*—Susan A. Loring
*Attorney, Agent, or Firm*—Whitham, Curtis, Whitham & McGinn

[57] ABSTRACT

The direct, concentrated local delivery of antibodies, and pooled human immunoglobulins in particular, to tissue surfaces (e.g., wounds, burns, etc.), and biomaterial implant surfaces significantly decreases the rate of infection at those sites and enhances healing. The immunoglobulins serve to opsonize circulating infectants for phagocytosis and killing, prior to microbial adhesion and biofilm formation, and neutralize bacterial toxins. The treatment methodology results in reduced inflammation, reduced complement and tissue damage, and reduced rejection of biomaterials and transplants.

14 Claims, No Drawings

PUBLICATIONS

Horan et al., "Pathogens Causing Nosocomial Infections", Antimicrobic Newsletter, vol. 5, No. 9, Sep. 1988, pp. 66–68.

MedImmune, Inc. 1991 Annual Report.

Pirofski et al., "Current State of the Hybridoma Technology", Journal of Clinical Immunology, vol. 10, No. 6 (Nov. Suppl. 1990), pp. 5S–14S.

Dwyer, "Manipulating the Immune System With Immune Globulin", New England Journal of Medicine, vol. 326, No. 2, Jan. 9, 1992, pp. 107–116.

Givner, "Human Immunoglobulins for Intravenous Use . . . ", Pediatrics, vol. 86, No. 6, Dec. 1990, pp. 955–962.

Steinman, "The Use of Monoclonal Antibodies for Treatment of Autoimmune Disease", Journal of Clinical Immunology, vol. 10, No. 6, (Nov. 1990 Supp) pp.30S–39S.

Waldmann et al. "Lymphokine Receptor–Directed Therapy: A Model of Immune Intervention", Journal of Clinical Immunology, vol. 10, No. 6 (Nov. 1990 Supp) pp. 19S–29S.

Vitetta, "Immunotoxins: New Therapeutic Reagents for Autoimmunity, Cancer and AIDS", Journal of Clinical Immunology, vol. 10, No. 6 (Nov. 1990 Supp), pp.15S–18S.

"Investment Opinion and Summary", Smith Barney, Aug. 31, 1992.

Gristina et al., "Microbes, Metals, and Other Nonbiological Substrata in Man", Orthopaedic Infection, W.B. Saunders Co., 1989, Chapter 3, pp. 26–36.

Gristina et al., "Microbial Adhesion and the Pathogenesis of Biomaterial–Centered Infections", Orthopaedic Infection, W.B. Saunders Co., 1989, Ch 2, pp.3–25.

Gristina et al., "Biomaterial–Centered Infections: Microbial Adhesion versus Tissue Integration", Pathogenesis of Wound and Biomaterial–Associated Infections, Springer–Verlag, pp. 193–216.

Anwar et al., "Effective Use of Antibiotics in the Treatment of Biofilm–Associated Infections", ASM News, vol. 58, No. 12, 1992, pp. 665–668.

Casadevall et al., "Serum Therapy Revisited: Animal Models of Infection and Development of Passive Antibody Therapy" Antimicrobial Agents and Chemotherapy, Aug. 1994, pp. 1695–1702.

Collins, M.S. et al. Infection, 15 Suppl. 2:551–559, 1987.

Sherertz et al., "Efficacy of Antibiotic–Coated Catheters in Preventing Subcutaneous Staphylococcus aureus Infection in Rabbits," Journal of Infectious Diseases, 167:98–106, 1993.

Seligson et al., "The Use of Antibiotic–Impregnated Polymethylmethacrylate Beads to Prevent the Evolution of Localized Infection," Journal of Orthopedic Trauma, vol. 6 No. 4, pp. 401–401 (1992).

Collins et al., "Therapy of Experimental Pseudomonas aeruginosa burn wound sepsis with human immunoglobulin G, Pseudomonas hyperimmune immunoglobulin G, and antibiotics," The Pathophysiology of Combined Injury and Trauma, Eds. Gruber, Walker, MacVittie and Conklin, Academic Press, 1987.

Norden, "Osteomyelitis: Lessons from Animal Models and Clinical Application," Musculoskeletal Infection Eds. Esterhai, Gristina, Poss, American Academy of Orthopaedic Surgeons, Dallas, Texas, 1990.

Norden, "Lessons Learned from Animal Models in Osteomyelitis," Review of Infectious Diseases, Jan.–Feb. 1988, 103–110.

Rissing, "Animal Models of Osteomyelitis," Infectious Diseases Clinics of North America, Ed. Norden, W.B. Saunders Co., Sep. 1990.

Andriole, "A Paradigm of Human Chronic Osteomyelitis," The Journal of Bone and Joint Surgery, vol. 55–A, No. 7, Oct. 1973.

Whalen, "A Histological Study of Acute Hematogenous Osteomyelitis following Physical Injuries in Rabbits," The Journal of Bone and Joint Surgery, pp. 1383–1392 Oct., 1988.

Worlock, "The Prevention of Infection in Open Fractures," The Journal of Bone and Joint Surgery, pp. 1341–1347, Oct. 1988.

Ramisse et al, "Passive Local Immunotherapy of Experimental Staphyloccal Pneumonia with Human Intravenous Immunoglobulin," Journal of Infectious Diseases 168:1030–3, 1993.

Costerton et al, "Behaviour of Bacteria in Biofilms" ASM News vol. 55, No. 12, 1989, pp. 650–654.

Georg Peters "New Considerations in the pathenogenesis of coagulase–negative staphylococcal foreign body infections" Journal of Antimicrobial Chemotherapy (1988) 21, Suppl. C. 139–148.

Tsukayama et al., "Microbiology of Prosthetic–Joint Infections," Complications in Orthopedics Nov./Dec. 1993, pp. 70–74.

Cheml, "Role of Monoclonal Antibody Therapy in the Treatment of Infectious Disease," American Journal of Hospital Pharmacy vol. 47, Nov. 1990 Supp 3 pp. S11–S15.

Hall, "IL–12 Holds Promise Against Cancer, Glimmer of AIDS Hope," Science, vol. 263, Mar. 25, 1994, pp. 1685–1686.

METHODS AND COMPOSITIONS FOR PASSIVE IMMUNOTHERAPY

CROSS-REFERENCE TO RELATED APPLICATIONS

This patent application is a continuation-in-part (CIP) patent application of the patent application filed Aug. 25, 1994, having U.S. Ser. No. 08/295,482, now U.S. Pat. No. 5,505,945, which itself is a continuation of the patent application filed Jan. 12, 1993, having U.S. Ser. No. 08/003,305, now abandoned, and the complete contents of the above-mentioned patent application files is herein incorporated by reference.

This invention was made with government support under AR26957 and GM35939, both of which were awarded by the National Institutes of Health. The government has certain rights in the invention.

BACKGROUND OF THE INVENTION

1. Field of the Invention

The invention is generally related to the in-situ use of immunoglobulins, antibodies, and antisera directly and locally applied at sites of possible infection to prevent and treat microbial adhesion and colonization of surgical and traumatic wounds, burns, biomaterials, damaged tissues, and organ and tissue transplants including auto-, allo-, and xenografts in man and animals.

2. Description of the Prior Art

Despite the widespread use of antibiotics, surgical wound infection, especially biomaterial centered wound infection (e.g., catheters, implants, etc.), or sepsis subsequent to major trauma with bacterial contamination is a significant worldwide problem in terms of both morbidity and treatment costs. Antibiotics tend not to be effective against contaminated open fracture, biomaterial centered, foreign body and burn infections because there is significant microbial adhesion to damaged tissue or biomaterial substrata, and the adhered microbes form bacterial biofilms which shield the microorganisms from the antibiotics. Furthermore, antibiotics cannot be extensively or exclusively used in a "preemptive" manner since the "use" of the antibiotics allows for the natural selection of antibiotic resistant strains of bacteria, which has resulted in the extensive and expanding development of antibiotic resistant strains as causes of infection.

Much research effort has been invested in determining methodologies for promoting and augmenting host defense mechanisms. In a simplified host defense scheme, invading bacteria are identified by complement and immunoglobulins, as well as additional proteins (all of which can be referred to as "matrix proteins" and "natural antibodies"), and are opsonized. After opsonization, the bacteria are phagocytized and destroyed by the cellular immune system and white blood cells (neutrophils and macrophages, etc.). Augmenting the host defenses in many clinical settings may be preferable or complementary to the use of antibiotics.

In the last decade, intravenous immunoglobulins (IVIG) have become an important treatment regime for bacterial and viral infections and of primary and secondary immunodeficiency states. For example, Buckley et al., *New Eng. J. Med.* 325:110–117 (1991) have reported using IVIG in the treatment of immunodeficiency diseases, and Commetta et al., *New Eng. J. Med.* 327:234–239 (1992) have described the prophylactic intravenous administration of standard immune globulin and core-lipopolysaccharide immune globulin in patients at high risk of post-surgical infection. IVIG is prepared from the pooled plasmas of large numbers of donors, and tend to have a broad representation of antibodies. Pooled polyvalent human globulins usually contain antibodies for ubiquitous pathogens such as *H. influenza* type B, pneumococci, staphylococci, diphtheria, tetanus, respiratory syncytial virus (RSV), measles, cytomegalovirus (CMV), varicella zoster virus, etc. Antibody concentrations vary from lot-to-lot and between manufacturers. IVIG therapy has been reported to be beneficial for many diseases produced by autoimmune immunopathologic mechanisms. Passive immunization against infections has been particularly successful with immune globulins specific for tetanus, hepatitis B, rabies, chickenpox, and cytomegalovirus. Passive immunization depends on the presence of high and consistent titers of antibodies to the respective pathogens in each preparation. Thus, while intravenous passive immunization has been successful for certain diseases, it has had inconsistent performance against many other types of infections, and particularly nosocomial infections derived from a hospital or clinical setting. Serum dilution, catabolic effects and decreased blood supply at surgical and trauma sites are among the reasons for the failure of IVIG in the treatment of wound infections and sepsis.

U.S. Pat. No. 4,412,990 to Lundblad et al. shows one example of an intravenous pharmaceutical composition containing immunoglobulin (IgG). Lundblad et al. shows that incorporating fibronectin in the solution results in synergistic opsonic activity that enhances phagocytosis of bacteria, immune complexes, and viruses.

IVIG products are commercially available from Baxter Healthcare and the American Red Cross.

Despite the advantages of IVIG, bacterial biofilms discussed above also shield microorganism from host defenses (antibodies, immunoglobulins, macrophages, etc.), and this results in the formation of an immunoincompetent inflammatory zone at damaged tissues and biomaterial interfaces. Biomaterial surfaces, their particulate debris, severe tissue trauma, and burns cause massive and chronic inflammatory responses characterized by host defense mechanism exhaustion. It has been reported that IVIG has been largely ineffective in the treatment of burn centered infections.

Immunoglobulins and antibody compositions have not been routinely delivered directly to the site of an infection. Three examples of such treatment schemes can be found in U.S. Pat. No. 4,994,269 to Collins et al., U.S. Pat. No. 4,714,612 to Nakamura et al., and Ma et al., *Arch. Oral Biol.*, 35 suppl:115S–122s, 1990. Collins et al. discloses the topical use of monoclonal antibodies for the prevention of experimental *Pseudomonas aeruginosa* lung infections. Specifically, the antibodies are administered via aerosol spray to the lungs. Results show beneficial effects in the prevention of pneumonia. Nakamura et al. discloses the use of a non-specific gamma globulin IgG in a mouthwash for preventing gingivitis. A scheme similar to Nakamura et al. is described in Ma et al. wherein monoclonal antibodies specific for *Streptococcus mutans* are combined with a mouthwash. Experiments showed control subjects experienced recolonization with *Streptococcus mutans* within two days, but those treated with monoclonal antibodies remained free of *Streptococcus mutans* for up to two years. One common feature of Collins et al., Nakamura et al., and Ma et al. is that the antibodies or immunoglobulins are delivered to a healthy tissue non-traumatized site which is external to the body (e.g., lungs and throat) which is not akin to a closed abscess wound, biomaterial implant site, or burn site, or to an implant (biomaterial surface).

SUMMARY OF THE INVENTION

It is an object of this invention to provide new methods and compositions for the direct, concentrated local delivery of passive immunity to damaged tissue (closed and open wounds), biomaterial implants and implant sites, and transplanted organs and tissues.

According to the invention, compositions containing antibodies to infectious agents are applied directly to damaged tissue, biomaterial surfaces, and transplant surfaces. Positioning the compositions at these sites allows bacteria to be pre-opsonized in-situ for enhanced phagocytosis and killing, and neutralization of toxins produced by microbes. The compositions can take the form of a creme, ointment, coating, layer with immobilized antibodies (e.g., gelatin, fibrin, cellulose, polymers, etc.), lavage fluid, injectable fluid, or the like. The compositions can contain immunoglobulins (IgG, IgA, and/or IgM), monoclonal antibodies, or hyperimmune serum. Pooled human immunoglobulin preparations are preferred because they contain antibodies to a wide spectrum of contemporary microorganisms. The immunoglobulin compositions may contain IgG, similar to an IVIG composition, or may contain a full repertoire of multiple class immunoglobulins (IgG, IgA, and IgM) since local use of the immunoglobulins will not give rise to the side effects normally associated with intravenous administration of IgA and IgM. The immunoglobulin compositions may be supplemented with monoclonal antibodies specific for certain infectants of interest, or be prepared in combination with pooled hyperimmune serum raised against certain infectants. Alternatively, hyperimmune serum or cocktails of two or more monoclonal antibodies can be used as the source of antibodies in the anti-infective composition of the present invention.

The compositions should be applied to the surfaces of tissues or biomaterials before or within six hours after the time of trauma or of cleaning or debridement of the wound or burn site, and prior to biofilm formation, so that bacteria present therein or arriving at the site will be pre-opsonized for phagocytosis and killing prior to their adhesion, invasion, replication and potential toxin production. Furthermore application prior to biofilm formation reduces the adhesion and colonization of infectious bacteria to certain tissues and biomaterials, and helps prevent the formation of a biofilm that would otherwise shield infectious bacteria from circulating immunoglobulins, macrophages, and antibiotics. In addition, having the antibodies in place will allow for neutralization of bacterial toxins that are released from living or dead bacteria. Biomaterial implants, such as catheters, bone screws and other fixation devices, artificial joints (hips, shoulders, etc.), artificial hearts, contact lenses, and vascular grafts, will ideally be coated with an antibody containing composition prior to implantation. This can be performed by pre-coating these devices at a manufacturing or packaging facility with the antibody composition, or by coating the devices after they are removed from packaging just prior to installation in the patient, or both. Organs (e.g., hearts, livers, etc.) or tissues (skin, vascular grafts, etc.) preferably will be coated with the antibody composition just prior to transplantation in a patient.

In addition, the antibody containing compositions may ideally be immobilized on a matrix material such as gelatin, fibrin, cellulose, chitosan, etc. Immobilizing the antibodies will provide the advantage of having a sustained level of antibodies at the site of trauma or biomaterial implant for a long period of time. Furthermore, coatings in which antibodies are immobilized may be a more convenient and appropriate manner for coating certain biomaterial implants. In some specific applications, the antibodies can be immobilized on a body contacting bandage, or immobilized on the surface of a catheter, or be immobilized on a dental implant, tampon, suppository, or lozenge. Immobilizing the antibodies onto the matrix material can be achieved by a number of different mechanisms including ionic attraction, co-mixing of antibodies with matrix material, etc.

DETAILED DESCRIPTION OF THE PREFERRED EMBODIMENTS OF THE INVENTION

The experiments discussed below in the Examples section demonstrate that compositions containing antibodies, when placed in-situ on a wound or biomaterial surfaces, can effectively inhibit microbial adhesion and colonization and reduce or eliminate the occurrence of bacterial infection in vivo. The methodology is effective against both gram positive and gram negative organisms, as well as multiple class and multiple strain bacterial (polymicrobial) challenges. *Staphylococcus aureus, Pseudomonas aeruginosa,* and *Streptococcus epidermidis* infections in particular were tested due to their ubiquitous nature, and due to the fact that these organisms are the source of a large magnitude of the hospital generated nosocomial infections found in patients. Pooled human immunoglobulin and hyperimmune serum raised against specific pathogens were utilized in the experiments. Depending upon the application, the compositions contemplated by this invention could include pooled immunoglobulins (IgG alone or in combination with IgA and IgM), pooled immunoglobulins supplemented by immunoglobulins obtained from patients hyperimmunized with a specific pathogen, pooled immunoglobulins supplemented with monoclonal antibodies directed to a specific infectant, pooled immunoglobulins obtained only from hyperimmunized patients, or mixtures of one or more monoclonal antibodies directed against specific infectants. IgA and IgM can be employed in the compositions because they are used locally, not systemically, according to the inventive methodology, and would not cause patient difficulties such as allergic reactions or anaphylactoid shock. In fact, using the full repertoire of immunoglobulins including IgG, IgA and IgM may provide certain benefits in reducing microbial adhesion (IgA) and in neutralizing microbial endo- and exotoxins (IgM), and in neutralizing complement driven tissue damage, thus also enhancing wound healing.

It is contemplated that the antibody compositions can be tailored to specific patients, and specific clinical conditions. For example, patients in hospitals in the U.S. may be exposed to one set of flora, while patients in hospitals in Europe might be exposed to another set. To combat microbial infections in the two different hospital settings, it is advantageous to use pooled human immunoglobulins from U.S. patients in the U.S. hospitals, and pooled human immunoglobulins from European patients in European hospitals. In addition, certain infectants are more commonly found in burn and open fracture wounds (e.g., *Staphylococcus aureus, Staphylococcus epidermidis, Pseudomonas aeruginosa,* clostridial sp., and enterobacter sp.), while other infectants are more commonly found on catheters and other implantable devices (e.g., Streptococci, *Candida albicans, Eschericia coli*) (note that *Staphylococcus aureus, Staphylococcus epidermidis,* pseudomonas sp. and enterobacter sp. are also concerns on catheters and/or other biomaterials). Thus, it is expected that a pooled immunoglobulin composition will be advantageously supplemented with monoclonal antibodies against a particular infectant of interest or immunoglobulins obtained from patients hyperimmunized with the particular infectant.

The Examples below demonstrate that the in-situ use of antibodies is highly effective against bacterial challenges by large numbers of bacteria, even when only small amounts of antibodies are used. Preferably, the compositions of this invention will comprise antibodies (monoclonals and/or immunoglobulins) between 0.5 to 50,000 mg/dl. Most preferably, the antibodies will be pooled human immunoglobulins and will be present between 1–10,000 mg/dl. The antibodies can be present in a liquid carrier such as a lavage fluid, saline wash, etc.; a creme or ointment carrier such as oleaginous bases or polyethylene glycol, etc.; a gel such as Duoderm® (Convatec); or a powder such as starch, alginates, gelatin, and cellulose. The antibodies may also be combined with and/or immobilized on matrix materials such as gelatin, cellulose, chitosan, chitin, fibrin, or the like. Immobilization can be achieved by a wide variety of techniques including mixing the matrix material together with the antibodies and allowing the matrix material to set thereafter, ionic attractions, etc.

The Examples demonstrate that the antibodies should be applied to the tissue or biomaterial surfaces prior to microbial adhesion and colonization. Thus, antibodies are in place to pre-opsonize infectants for phagocytosis and killing. Best results are achieved when the antibody compositions are applied to the tissue surfaces at the time of trauma or surgery, or contamination, or within six hours after trauma or within six hours after cleaning the traumatized site. In the case of biomaterial implants (e.g., catheters, bone screws, artificial hearts, artificial joints, etc.), the surfaces of the biomaterials can be coated with an antibody composition just prior to installation. Alternatively, the biomaterial surfaces can be coated at the time of manufacturing and prior to packaging. The antibodies may be advantageously immobilized directly on the biomaterial surface using gelatin, fibrin, collagen, cellulose or the like. In organ and tissue transplantation, it is recommended that the organ or tissue be dipped in an antibody containing composition or otherwise coated or perfused with antibodies just prior to transplantation into the patient's body.

Pre-coating with antibodies may be particularly advantageous in animal tissue to human transplants, wherein the tissue or organ is coated prior to implanting in a patient. The antibodies, in addition to opsonizing circulating or ambient infectants, may assist in tissue integration (acceptance of the transplant).

It is expected that the compositions and methodologies described herein will be useful in the treatment of both humans and animals.

The treatment of certain clinical situations is discussed below for exemplary purposes. However, it should be understood that the methodologies of this invention can be practiced in a wide variety of different clinical settings.

Wounds

Open wounds on the skin or deep tissue surfaces will be cleaned and then coated with the antibody compositions (preferably within six hours and before biofilm formation). The antibody compositions will preferably contain monoclonal antibodies or immunoglobulins in a creme or gel matrix which can be spread onto the surface of the wound. Preferably the antibodies will be present at 200–5000 mg/dl for IgG, 40–1000 mg/dl for IgA (if included), or 20–500 mg/dl for IgM (if included), which is one fifth to five times as much as the center of the physiologic level for IgG, IgA, and IgM, respectively. Staphylococcus aureus, Pseudomonas aeruginosa, Eschericia coli, and clostridia are commonly encountered in open wounds. Thus, it would be advantageous to use pooled immunoglobulins which have been obtained from patients hyperimmunized with these microorganisms, or immunoglobulin compositions supplemented with monoclonal antibodies specific for these microorganisms. Alternatively, compositions containing only monoclonal antibodies could be used. Frequently, antibody levels may be lower than effective in vascularly ischemic, acute and chronic wounds, or at damaged tissue sites, or in immunocompromised patients, or in certain locations (organs, mucosal, and tissue sites). Under these conditions, it would be advantageous to have elevated levels of antibodies. Bandages may advantageously be employed in treating open wounds, where the bandages utilize antibodies coated or immobilized on the bandage surface. It is advantageous in situations where antibodies will be immobilized on a medium to use concentrations of antibodies selected for prolonged delivery. As discussed above, the immunoglobulins can be coated or immobilized on the bandage surface at the time of packaging, or simply be applied at the time of bandaging using a fluid, gel, creme, powder or the like.

Closed wounds can be coated with appropriate antibodies in saline or other fluid or creme carriers at the time of surgical closure. Preferably, immunoglobulins can be used as the antibodies and will be present at concentrated or physiologic levels (200–5000 mg/dl for IgG, 40–1000 mg/dl for IgA (if included), or 20–500 mg/dl for IgM (if included)). Included in this scheme would be closed space surgical procedures entered by endoscopic methods (e.g., arthroscope, bladder, peritoneal gall bladder, genitourinary and gastro-intestinal, spinal canal, central nervous system, etc.)

Burns

The antibodies, which are preferably immunoglobulins at concentrated or physiologic levels as set forth above, can be delivered at the time of injury, debridement or grafting by solution lavage, injection, cremes, and bandages. The antibodies may be applied directly to the burned or debrided tissue, or be applied on the surface of a skin graft or bandage. In the case of a bandage, the antibodies will be present in a matrix carrier at elevated concentrations designed for extended release (e.g., up to 500,000 mg/dl or more).

Implants

Catheters, total joints, fixation devices, pacemakers, central lines, contact lenses, vascular grafts, artificial hearts, pumps, diagnostic and monitoring devices, drug delivery devices, and devices including polymer packaged cells and/or therapeutics for protein or drug delivery, etc. may be lavaged or coated with antibodies at the time of surgery or during manufacture of the part using a wide variety of carriers and surface binding agents. Preferably, the antibodies are pooled immunoglobulins at physiologic or concentrated levels. The antibodies may be implanted in solid or liquid carriers or porous delivery devices of polymers, or in suppositories for localized internal delivery, or in biodegradable materials such as polylactides and liposomes for localized, graduated and prolonged delivery in wounds, organs, or body cavities. A particular device contemplated by this invention is an implantable porous device coated with immunoglobulins which also includes immunoglobulins present in the porous material for graduated delivery of immunoglobulins at the implant site.

Transplants

Auto, allo, and xeno-graft materials and organs (livers, heart, lungs, bones, tissues, skin, cartilage) may be suitably coated, perfused, or dipped in antibody compositions (e.g., pooled immunoglobulins) in various concentrations and classes as described above, thereby providing natural antibodies in appropriate concentrations where their presence may have been eliminated completely or in part by the processes involved in transplantation. The new, supplemented, or enhanced presence of immunoglobulins and/or monoclonal antibodies on transplant organ/tissue surfaces should immediately opsonize or otherwise inactivate contaminating or ambient microbes. Additional benefits of this process would be the inactivation or neutralization of toxins and the diminution of tissue damage by toxins and activated compliment proteins, as well as the diminution of local autoimmune, and non-self immune type reactions generated by transplanted tissues.

EXAMPLE 1

Experiments have been conducted with a closed abscess intradermal infection model (a severe challenge used for antibiotic testing) to demonstrate that the direct local application of antibodies, antisera and/or immunoglobulins (IgG, IgA, and IgM) to wounds before or immediately after (2–6 hours) bacterial contamination and before biofilm formation reduces microbial adhesion and enhances clearance by cell mediated host defenses and thus prevents infection. In the closed abscess model, rabbits are anesthetized and area of about 10 cm×15 cm on the back is shaved and depilated. A known cfu (ca. $10^6$) of bacteria suspended in 100 µl of saline is injected intradermally using a 26 gauge needle. On companion sites, the same cfu of bacteria is injected with known dilution of antiserum (typically pooled human IgG). The development of lesions was observed and the size of the lesion was recorded on a standard scale of 0 (no lesion or <5 mm diameter) to 5+ (>30 mm) on 5 mm increments.

In one experiment, a known number (8–9×$10^6$ cfu) of four different clinical isolates of S. aureus, received from Fair Oaks Hospital, Fairfax, Va., were suspended in 100 µl of saline, and were injected intradermally into depilated rabbits with a 26 gauge needle. The clinical isolates used were S. aureus #2002, S. aureus #4651, S. aureus #4855, and S. aureus #5848. On companion sites, the same doses of bacteria were injected together with 0.5 mg of Human Gamma Globulin (available from the Holland Research Laboratory of the American Red Cross). The size of the lesions was recorded four days after the date of injection. Table 1 shows that the sites injected with bacteria alone developed large expanded lesions, while sites injected with bacteria in the presence of human gamma globulin developed comparatively smaller lesions.

TABLE 1

| Bacterial Isolates | cfu Injected | Size of Lesions | |
|---|---|---|---|
| | | Control | Sites with HuGG |
| #2002 | 8 × $10^6$ | 3+ | Trace |
| #4651 | 8 × $10^6$ | 4+ | 1+ |
| #4855 | 9 × $10^6$ | 2+ | Trace |
| #5848 | 9 × $10^6$ | 3+ | 2+ |

In addition to the results in Table 1, it was observed that sites injected with bacteria alone developed signs of cellulitis, while those which received both bacteria and human gamma globulin did not develop signs of cellulitis.

The results in Table 1 indicate that the pooled human gamma globulin applied locally at the sites of bacterial challenge reduces the severity of infection caused by different clinical isolates of S. aureus. The use of multiple recent pathogen isolates suggests that contemporary pooled human IgG will be broadly effective against environmentally and nosocomially acquired infections.

In another exeriment, the injection of pooled human gamma globulin was demonstrated to effectively prevent simultaneous polymicrobial infections, wherein two different clinical isolates of S. aureus were injected at the same test site. Using the closed abscess intradermal infection model described above, S. aureus #2002 and S. aureus #4651 were each suspended in 100 µl of saline and injected intradermally into three test sites on the back of a depilated rabbit. On three companion sites on the back of the depilated rabbit, the same doses of bacteria were injected together with 0.75 mg of pooled human gamma globulin. Table 2 indicates that the sites injected with bacteria alone developed large expanded lesions and signs of cellulitis, while the sites injected with the bacterial mixture in the presence of human gamma globulin developed comparatively smaller lesions and did not develop signs of cellulitis.

TABLE 2

| | Appearance of Lesions | | |
|---|---|---|---|
| Treatments | Site 1 | Site 2 | Site 3 |
| (1) Bacterial Mixture alone | 3+ cellulitis | 3+ cellulitis | 3+ cellulitis |
| (2) Bacteria + HuGG | 2+ | 1+ | 0 |

The results in Table 2 indicate that pooled human gamma globulin applied locally at the sites of bacterial challenge reduces the severity of multiple infection caused by two clinical isolates of S. aureus. Effectiveness against polymicrobial infection indicates that contemporary pooled human IgG has broad spectrum antimicrobial activity at a mechanistic level circumventing microbial synergies.

In another experiment, the in-situ application of pooled human IgG was shown to be effective for preventing infection with various doses of P. aeruginosa (P. aeruginosa IFO 3455 obtained from the American Type Culture Collection). The closed abscess model described above was employed, and various infective doses were injected intradermally with or without 0.5 mg of human IgG per site. Lesion sizes were measured and recorded after 2 days. Table 3 shows a high level to complete inhibition of infection was observed when comparing the untreated to the treated sites.

TABLE 3

| Rabbit # | CFU injected | % Inhibition of infection |
|---|---|---|
| 07826 | 7 × $10^6$ | 70 |
| | 1.4 × $10^6$ | 85 |
| | 7 × $10^5$ | 100 |
| 07828 | 7 × $10^6$ | 100 |
| | 1.4 × $10^6$ | 100 |
| | 7 × $10^5$ | 100 |

In a similar experiment to that described above with P. aeruginosa IFO 3455, rabbits were injected with various infective doses of P. aeruginosa in the presence or absence of IgG (0.5 mg). The size of the lesions were meansured after 3 days. The lesions were excised, homogenized in sterile saline, and enumerated by plating on nutrient agar and colong counts. The results presented in Table 4 are indicated as ±SEM (N=3).

TABLE 4

| CFU Injected | no IgG | | With IgG | |
|---|---|---|---|---|
| | Lesion size (mm) | Bacterial Colonies (per site) | Lesion Size (mm) | Bacterial Colonies (per site) |
| $10^7$ | 75 ± 15 | 2,100,000 | 33 ± 9 | 1,800,000 |
| $10^6$ | 36 ± 10 | 490,000 | 4 ± 1 | 7,500 |
| $10^5$ | 7 ± 1 | 10,000 | 0 | 0 |

Tables 3 and 4 demonstrate that in-situ use of human gamma globulin inhibits infection from *P. aeruginosa*. Tables 3 and 4, in combination with Tables 1 and 2, demonstrate that a wide variety of infections can be prevented using the techniques contemplated by this invention.

In order to evaluate the dose dependency of the human IgG in combatting *P. aeruginosa* centered infection, four rabbits were injected intradermally with $1.5 \times 10^6$ CFU of *P. aeruginosa* IFO 3455 with or without various concentrations of IgG (human gamma globulin available from the American Red Cross). Each rabbit received two injections of the same treatment. The size of the lesions were measured after 3 days. Table 5 shows the average results for the four rabbits.

TABLE 5

| Concentration of IgG (mg) | % Inhibition |
|---|---|
| 0 | 0 |
| 0.1 | 38 ± 14 |
| 0.5 | 85 ± 12 |
| 1.0 | 95 ± 5 |

Table 5 shows that even small amounts of IgG (e.g., 0.5–1 mg) can be effective for inhibiting infection. Table 5 indicates that larger quantities of IgG were generally more effective. The amount of IgG to be used at any wound, trauma, burn, or implant site will depend upon the size and characteristics of the site, as well as the mode of application of the IgG.

In another experiment, the time of IgG application in preventing closed abscess intradermal infection by *P. aeruginosa* IFO 3455 in rabbits was evaluated. Rabbits were injected intradermally with $10^6$ CFU of *P. aeruginosa*. IgG (0.5 mg) was injected at the same sites after 0, 2, 4, 6, or 24 hrs. Control sites received saline at the same time intervals. Each rabbit had two sites with identical treatments. The size of the lesions was assessed after 3 days. The data in Table 6 represents the average of four lesions on two rabbits.

TABLE 6

| Time of IgG Application after bacterial infection (hr) | Lesion Size (mm) | % inhibition |
|---|---|---|
| 0 | 13 | 65 |
| 2 | 19 | 49 |
| 4 | 31 | 16 |
| 6 | 32 | 14 |
| 24 | 34 | 8 |
| No IgG | 37 | 0 |

Table 6 suggests that the immunoglobulins or antibodies should be applied to the wound, burn, or trauma site at the time of surgery or debridement or up to two–six hours thereafter.

EXAMPLE 2

Experiments were conducted which demonstrated that intradermal introduction of antibodies raised against formalin killed whole organism of *S. areus* and *P. aeruginosa* can prevent the formation of progressive infectious lesions after a bacterial challenge. In all of these experiments, the *S. aureus* (ATCC #25923) and *P. aeruginosa* (strain IFO 3455) were grown in trypticase soy broth overnight at 37° C. with agitation. The vaccine was prepared and the antisera were produced as follows:

First, formalin (0.3 ml/100 ml of culture) was added to the culture to kill the cells. The killed cells were obtained by centrifugation, washed and resuspended in saline containing 0.3% formalin. The suspension was stored at 4° C. New Zealand White rabbits were vaccinated intravenously twice a week (on Mondays and Fridays) for a period of four weeks with gradually increasing amounts ($10^9$ ml) of formalin killed cells which were suspended in 1–3 ml of saline. The sera were obtained from the rabbits 3–5 days after the last vaccination. The sera were then lyophilized and stored at between −20° C. and −60° C. The agglutination titers of the sera were approximately 1:2,560.

Prior to conducting the experiments, it was necessary to determine the dosage ranges of *S. aureus* and *P. aeruginosa* that produce a reproducible and consistent infectious lesion in the rabbit skin. The rabbits were prepared as described above. In order to determine the dose of *S. aureus*, several experiments were performed which revealed that doses of microorganisms between $5 \times 10^5$ and $5 \times 10^6$ suspended in 100 µl of saline consistently produced infectious lesions within 1–3 days. The infectious lesions were characterized by having a central core of pus and an elevation of about 4 mm. A similar set of experiments were performed with *P. aeruginosa* and it was found that consistent lesions were formed following intradermal injection of between $5 \times 10^5$ and $5 \times 10^6$ organisms in 10 µl of saline.

In one set of experiments, an area of about 10×20 cm on the backs of each of five rabbits was clipped and depilated. Six intradermal injections were administered on each rabbit in these areas. All of the sites were injected with a predetermined infectious dose of $5 \times 10^5$ and $5'10^6$ bacteria. Two of the sites were injected intradermally with an infectious dose of *S. aureus* and the specific antibody serum preparation (50 µl of a 1:5 dilution) which was obtained from rabbits hyperimmunized with formalinized *S. aureus* in a total volume of 150 µl. The second pair of sites were injected intradermally with equivalent amount of *S. aureus* and normal rabbit serum which was similarly prepared in a total volume of 150 µl. The final two sites were injected intradermally with an infectious dose of *S. aureus* and saline alone (no serum) in a total volume of 150 µl. All of the rabbits were monitored 3–4 days. At the end of this period, the injection sites were measured. The rabbits were euthanized and the individual lesions were cultured for residual numbers of *S. aureus*.

Table 7 shows that the antibody preparations specific for *S. aureus* were consistently effective in preventing the inoculum of *S. aureus* from establishing an infection, while, the sites that received normal serum preparations yielded numbers of *S. aureus* which exceeded the infectious dose.

TABLE 7

| Rabbit | Treatment | Inoculum | CFU[a] |
|---|---|---|---|
| 70507 | AS[b] | $2.5 \times 10^6$ | 0 |
| | NS[c] | $2.5 \times 10^6$ | Too numerous |
| 73705 | AS | $2.5 \times 10^6$ | 0 |
| | NS | $2.5 \times 10^6$ | Too numerous |

TABLE 7-continued

| Rabbit | Treatment | Inoculum | CFU[a] |
|---|---|---|---|
| 73951 | AS | $3.4 \times 10^6$ | 0 |
| | NS | $3.4 \times 10^6$ | Too numerous |
| 67463 | AS | NR[d] | 0 |
| | NS | NR | Too numerous |
| 70327 | AS | $4.5 \times 10^5$ | 0 |
| | NS | $4.5 \times 10^5$ | Too numerous |

[a]Colony forming units
[b]Antiserum against *S. aureus*
[c]normal rabbit serum
[d]not reliable Although not indicated in Table 7, the control sites also yielded numbers of *S. aureus* which were too numerous to count.

Another set of experiments similar to that described above was performed with *Pseudomonas aeruginosa*. In these experiments, approximately $5 \times 10^6$ of *P. aeruginosa* were injected intradermally in 100 μl. In addition, 50 μl of a 1:5 dilution of antiserum was injected at two sites, 50 μl of a 1:5 dilution of normal serum was injected at two sites, and saline was injected at two sites. The rabbits were monitored for three days, at which time they were euthanized and the lesions were measured, dissected, and cultured for residual *P. aeruginosa*.

Table 8 shows that the antiserum was effective in almost completely eradicating the inocula, one normal rabbit serum preparation had a sufficient amount of antibody against *P. aeruginosa* to partially eradicate the infection, and that when saline was administered with bacteria the number of colonies were too numerous to count.

TABLE 8

| Rabbit | Treatment | Inoculum | CFUs[a] |
|---|---|---|---|
| 76826 | AS[b] | $5 \times 10^6$ | 0 |
| | NS[c] | $5 \times 10^6$ | 17 |
| | Saline | $5 \times 10^6$ | Too numerous |
| 77134 | AS | $5 \times 10^6$ | 21 |
| | NS | $5 \times 10^6$ | Too numerous |
| | Saline | $5 \times 10^6$ | Too numerous |
| 34623 | AS | $7 \times 10^6$ | 0 |
| | NS | $7 \times 10^6$ | 190 |
| | Saline | $7 \times 10^6$ | Too numerous |
| 29040 | AS | $7 \times 10^6$ | 25 |
| | NS | $7 \times 10^6$ | Too numerous |
| | Saline | $7 \times 10^6$ | Too numerous |

[a]colony forming units
[b]antiserum against *P. aeruginosa*
[c]normal rabbit serum Another set of experiments was conducted in which sterilized polymethylmethacrylate (PMMA) beads (10–50 μm diameter) and latex (polystyrene microsphere latex) beads (approximately 25 μm in diameter) were included with the various preparations to determine the protective effect of specific antisera in the presence of a biomaterial or foreign body. The latex beads present a serious infectious challenge since they have high surface to volume ratios, and it is known that bacteria electively prefer to aggregate on the surfaces of implanted biomaterials.

On the back of the rabbit an infectious dose ($5.8 \times 10^6$) of *S. aureus* was intradermally injected in combination with both a hyperimmune serum against *S. aureus* and normal serum in the presence of PMMA beads (10–50 μm diameter). The sera were injected as 50 μl of a 1:5 dilution and the injection had a total volume of 150 μl. The development of lesions at the injection sites was recorded daily. Three days after injection, the lesions were excised, cultured on nutrient agar and the number of remaining viable bacteria was determined.

Table 9 shows that the sites inoculated with *S. aureus* and antiserum did not develop lesions or infection even in the presence of PMMA beads, while the sites inoculated with *S. aureus* and the normal rabbit serum in the presence of PMMA beads developed lesions and showed symptoms of infection with liquid pus, and cultures of the lesions resulted in colonies too numerous to count.

TABLE 9

| Rabbit | Treatment | Inoculum | CFUs |
|---|---|---|---|
| 70334 | Antiserum against *S. aureus* + PMMA | $5.5 \times 10^6$ | 0 |
| | Normal rabbit Serum + PMMA | $5.5 \times 10^6$ | Too large |

The experiments reported in Table 9 were repeated using latex beads in place of PMMA beads. In this experiment, the back of a rabbit was intradermally injected with an infective dose ($4 \times 10^5$) of *S. aureus* in combination with a hyperimmune serum (50 μl of 1:5 dilution) or with normal rabbit serum (50 μl of a 1:5 dilution) in the presence of latex beads (approximately 25 μm diameter, $1.5 \times 10^4$ beads) in a total volume of 150 μl. The development of the lesions at the injection sites was recorded daily. Four days after injection, the lesions were excised, cultured on nutrient agar and the number of viable bacteria was determined.

Table 10 shows that the sites inoculated with *S. aureus* and specific antiserum in the presence of the latex beads did not develop any infectious lesions as confirmed by a total sterilization of the inoculum. In contrast, the sites that received the normal rabbit sera, *S. aureus* and latex beads developed large (5+) infectious lesions that contained a large relative volume of pus. The cultures of these lesions revealed too many colonies to count.

TABLE 10

| Rabbit | Treatment | Inoculum | CFUs |
|---|---|---|---|
| 71033 | Antiserum against *S. aureus* + latex | $4 \times 10^5$ | 0 |
| | Normal rabbit Serum + latex | $4 \times 10^5$ | Too numerous |

Additional experiments were conducted with *P. aeruginosa* which were identical to the PMMA and latex bead experiments with *S. aureus*, with the exception that the dilutions of the hyperimmune and normal sera were 1:50 instead of 1:5. In addition, PMMA particles (10–50 μm; $1 \times 10^3$) or latex particles (ca. 25 μm; $1.5 \times 10^3$) were introduced with the inoculum. The total volume was 150 μl. Table 11 shows the results of these experiments, and indicates that the hyperimmune serum markedly suppressed the infection in the presence of PMMA or latex particles.

TABLE 11

| Rabbit | Treatment | Particle | Inoculum | CFUs | Lesion |
|---|---|---|---|---|---|
| 29115 | AS[a] | PMMA | $5 \times 10^6$ | 2 | 0 |
|  | NS[b] | PMMA | $5 \times 10^6$ | 172 | 3+ |
|  | AS | Latex | $5 \times 10^6$ | 7 | Trace |
|  | NS | Latex | $5 \times 10^6$ | Too many | 4+ |
| 29024 | AS | PMMA | $5 \times 10^6$ | 4 | 0 |
|  | NS | PMMA | $5 \times 10^6$ | 262 | 3+ |
|  | AS | Latex | $5 \times 10^6$ | 28 | 0 |
|  | NS | Latex | $5 \times 10^6$ | 50 | 2+ |

[a]antiserum against *P. aeruginosa*
[b]normal rabbit serum

Similar experiments to those described above in connection with Tables 10–11 were performed to determine the effect of antiserum against *S. aureus* in the presence of titanium particles (1–3 µm; $1 \times 10^3$) or in the presence of latex particles (ca. 25 µm; $1.5 \times 10^3$). These were prepared in a final volume of 150 µl. Table 12 shows that the antiserum against *S. aureus* is effective in preventing infection.

TABLE 12

| Rabbit | Treatment | Particle | Inoculum | CFUs | Lesion |
|---|---|---|---|---|---|
| 29071 | AS[a] | Titanium | $2.4 \times 10^6$ | 0 | 0 |
|  | NS[b] | Titanium | $2.4 \times 10^6$ | Too many | 3+ |
|  | AS | Latex | $2.4 \times 10^6$ | 6 | 0 |
|  | NS | Latex | $2.4 \times 10^6$ | Too many | 2+ |
| 24116 | AS | Titanium | $2.4 \times 10^6$ | 2 | 0 |
|  | NS | Titanium | $2.4 \times 10^6$ | Too many | 3+ |
|  | AS | Latex | $2.4 \times 10^6$ | 0 | 0 |
|  | NS | Latex | $2.4 \times 10^6$ | 27 | 2+ |

[a]antiserum against *S. aureus*
[b]normal rabbit serum

An experiment was also carried out using the RP12 strain of *S. epidermidis* in a protocol similar to the one described above in connection with Table 12. Approximately $2 \times 10^6$ *S. epidermidis* cells in 50 µl of saline were mixed with 50 µl of anti-*S. epidermidis* antiserum and PMMA particles (ca. 10–50 µm in diameter; $1 \times 10^3$) in 50 µl to give a total injection volume of 150 µl. This study also showed that the antiserum specific for *S. epidermidis* prevented an infection by *S. epidermidis*, even in the presence of PMMA particles.

In additional experiments, standard suspensions of the RP12 strain of *S. epidermidis* were incubated for 30 minutes in 1:200 dilutions of either normal rabbit serum or hyperimmune serum against RP12 strain of *S. epidermidis*. This allowed the specific antibodies to bind to the surface polysaccharide molecules of the organisms. These suspensions were washed with phosphate buffered saline (PBS) and standard samples of PMMA were added to the various preparations. The bacteria-PMMA preparations were incubated for sixty minutes, and the PMMA samples were then washed three times with PBS to remove loosely attached bacteria the PMMA samples were sonicated for 10 minutes in PBS and the supernatants were diluted and plated on tripticase-soy agar to determine the number of colony forming units that adhered to the PMMA samples. Table 13 shows that normal serum has some inhibitory effects, but that the antiserum had significantly greater inhibitory effects.

TABLE 13

| PMMA plus RP12 incubated with: | CFU Bound To PMMA | Percent Inhibition |
|---|---|---|
| PBS | 393,000 | 0 |
| Normal Serum | 319,000 |  |
| Antiserum (1:200; lot 11949) | 105,000 | 67[a] 73[b] |

[a]Calculated as the percent inhibition of anti-sera treated RP12 versus RP12 pretreated with normal sera
[b]Calculated as the percent inhibition of anti-sera treated RP12 versus RP12 pretreated with only PBS The IgG fraction was isolated from the antiserum (11949) and tested for its capacity to block adherence of the RP12 strain. PMMA samples incubated with RP12 suspended in PBS (no antibodies) bound 604,000 CFU per sample. In sharp contrast, PMMA samples incubated with RP12 preincubated with hyperimmune IgG only bound 33,000 organisms. This represents a 94% inhibition of binding of RP12 to PMMA.

For comparison purposes, experiments were conducted to determine the capacity of antiserum (11949) to inhibit the binding of various strains of coagulase negative staphylococci. Six strains of coagulase negative staphylococci were incubated with the anti-RP12 antiserum (11949) to determine whether specificity exists with respect to blocking the adherence of the different strains to PMMA. Table 14 shows the results for each strain.

TABLE 14

| Strain | CFU/Sample | % Inhibition |
|---|---|---|
| RP12 | 198,000–6,000 | 67–99% |
| SP2 | 162,000 | 73 |
| SE360 | 602,000 | 0 |
| LD1 | 126,000 | 79 |
| ERI | 610,000 | 0 |
| RP162A | 695,000 | 0 |

The results in Table 14 indicate that there is specificity in inhibition and that serologic groups of adhesins exist.

Collectively, the experiments set forth in this example demonstrate that delivery of antibodies in situ into a wound site, and particularly a closed abscess wound, are highly effective as a prophylactic treatment in eradicating bacteria (in excess of 5 million). The intradermal wound model is a severe test for this treatment methodology because it is representative of a closed infected wound, which is the most difficult to treat and control. The in situ use of the antiserums were effective in preventing infections caused by both representative gram negative bacterium (*P. aeruginosa*) as well as two representative gram positive bacterium (*S. aureus* and *S. epidermidis*).

EXAMPLE 3

Experiments were conducted to demonstrate that pooled human immunoglobulins could be effectively used to prevent *Pseudomonas aeruginosa* infection where the *Pseudomonas aeruginosa* is associated with a titanium wire. In the experiments, the bacteria employed were *Pseudomonas aeruginosa* IFO 3455, and the foriegn body was a titanium wire measuring 10 mm in length and 0.8 mm in diameter. Binding of the *Pseudomonas aeruginosa* to the titanium wire was achieved by culturing the bacteria for 6 hrs to the log phase and washing and resuspending in saline to obtain approximately $10^8$ CFU/ml, and incubating pieces of titanium wires in the bacterial suspension for 60 min. at 37° C. The wires were washed to remove loosely attached bacteria. To determine the number of bacteria attached on a titanium wire sample, wires were sonicated in 1 ml of saline in a water-bath sonicator to release the bacteria into saline, and the bacterial suspensions were subsequently serially diluted and plated. On average, the number of bacteria attached to the titanium wire samples was $10^5$.

One batch of contaminated wires were implanted intradermally and another batch of wires were dipped in IgG solution (10 mg/ml) before implantation. The IgG solution was obtained from Baxter, International Hyland Division, and was solvent-detergent treated for viral safety. The treated and untreated wires were implanted in the same rabbit on its back such that side-by-side comparisons could be easily made. The rabbits were anesthetized and an area of 10 cm×15 cm was shaved and depilated. The wire was implanted into the intradermal region using a 14 gauge needle attached to a syringe with a plunger that pushes the wire from inside the needle into the intradermal region. The development of lesions was observed daily and the size of the lesion was recorded five days after implantation. Three rabbits in total were tested. Table 15 shows that the untreated contaminated titanium wires produced large lesions, whereas the contaminated titanium wires that had been dipped in IgG solution prior to implantation produced significantly smaller lesions.

TABLE 15

| | Lesion (mm) | | % |
|---|---|---|---|
| Rabbit # | No IgG | With IgG | Inhibition |
| 06301 | 70 | 7.5 | 89 |
| 06302 | 40 | 5 | 87 |
| 06349 | 10 | 1.5 | 85 |

Table 15 shows that the size of the lesion resulting from a contaminated titanium wire implanted into an animal can be reduced by 85% or more if the wire is coated with immunoglobulin or antibodies (e.g., IgG) prior to implantation. The results indicate that implantable devices, such as catheters, artificial hearts, hip and shoulder and other joint replacements, bone screws, etc., would benefit from prior treatment with immunoglobulin and antibody solutions.

In a similar test, Pseudomonas aeruginosa contaminated titanium wires were intradermally implanted into depilated regions of a rabbit's back. Some of the implantation sites were treated by injecting IgG solution (10 mg/ml) adjacent the wires. It was observed that this treatment methodology was also effective in reducing infection, as determined from a comparison of lesion sizes. However, coating of the titanium wire was a more effective treatment methodology thant injecting immunoglobulins at the site of implantation. Hence, it is preferred that the implantable device be coated with a immunoglobulins or antibodies prior to implantation. Coating of the implantable device can be achieved by dipping the device in a liquid solution, creme, ointment, or the like. In certain situations, it may be advantageous to both coat the implantable device prior to implantation, and to treat the region in which the device will be implanted.

EXAMPLE 4

Experiments were conducted to demonstrate that prior treatment with immunoglobulin or antibody solutions could be used to prevent the adherence of certain organisms to foriegn bodies. Specifically, the of human IgG on the adherance of P. aeruginosa and S. aureus to titanium wire was evaluated. Clean and autoclaved titanium wires (10 mm×0.8 mm; Aldrich Chemical Company) were incubated with IgG solution (1 or 10 mg/ml; available from Baxter, International Hyland Division) for 30 min. at 37° C. After incubation, the wires were washed to remove excess IgG. Control wires were incubated in saline solution. Subsequently, the wires were incubated with bacterial suspensions (108 CFU/ml) for 1 hr at 37° C. The wires were washed to remove loosely attached bacteria. The wires were sonicated in 1 ml of saline to release the bacteria into the saline solution, and they were serially diluted and plated. Table 16 shows that coating of titanium wires with IgG inhibited the binding of S. aureus on a dose dependent manner, however, it did not inhibit the binding of P. aeruginosa.

TABLE 16

| Bacteria | Conc. of IgG (mg/ml) | Bacteria bound/wire | % Inhibition |
|---|---|---|---|
| S. aureus | 0 | 68,000 | 0 |
| | 0.1 | 40,000 | 41.2 |
| | 1.0 | 18,000 | 73.6 |
| | 10.0 | 13,000 | 80.9 |
| P. aeruginosa | 0 | 320,000 | 0 |
| | 10 | 450,000 | 0 |

Table 16 demonstrates that pretreatment of implantable foriegn bodies with immunoglobulins and antibody compositions can prevent the adherence of some common infectious agents such as S. aureus.

EXAMPLE 5

The inhibition of P. aeruginosa intradermal infection in rabbit using pooled human immunoglobulins in the presence of Duoderm hydroactive gel available from Convatec, Princeton, N.J., was investigated. The experiment demonstrated that the immunoglobulins were effective in gel carriers. It should be understood that the immunoglobulin compositions of the present invention can be used in a wide variety of carrier materials including syrups, ointments, cremes and gels. In the experiments, DuoDerm hydroactive gel was mixed with sterile saline to make it injectable. Pooled human IgG, at 0.5 mg/site, was injected intradermally in combination with the DuoDerm hydroactive gell and 106 CFU of P. aeruginosa. The lesion size was measured after four days. In the one rabbit tested, the size of the lesion at the site injected with bacteria and gel was 28 mm, while the size of the lesion at the site injected with bacteria, gel, and IgG was only 15 mm.

One of our on going animal experiment seems to indicate that pooled human IgG applied locally with Duoderm Hydroactive gel in full thickness 'slit wound' can reduce bacterial infection as well as enhance wound healing.

Back of rabbit were shaved and depilated. Shaved surfaces were cleaned with 70% ethanol. Six one cm long full thickness incisions were made. P. aeruginosa ($10^7$ CFU in 10 μl of saline) were injected into two of the wounds. Duoderm gel was applied into two of the sites and subsequently injected with bacteria. The last two sites were applied with Duoderm gel containing 50 mg of IgG in gm gel and subsequently inoculated with bacteria. The development of lesions and the effect of gel and IgG on the lesion and wound healing was observed and recorded.

Infection was developed in 2 days. The sites that received bacteria or bacteria plus gel developed large lesions and the sizes were comparable. The sites that received bacteria plus gel plus IgG developed comparatively smaller lesions. Ten days post challenge the lesions grew larger, however, the IgG significantly inhibited the infection. No further enlargement of lesion size was observed by day 20. Interestingly, the sites injected with IgG had smaller lesions and seemed to heal faster than other sites.

EXAMPLE 6

Table 17 lists the major candidates for prophylaxis and treatment of wound, burn, nosocomial, oral and respiratory infections, and biomaterial centered infections of all types.

TABLE 17

| Microorganism | Estimated Effective Conc. Of Specific Antibodies |
| --- | --- |
| Staphylococcus aureus | 1–50 µg/ml |
| S. epidermidis | 1–50 µg/ml |
| Coagulase Neg. Staph. | 1–50 µg/ml |
| Streptococcus (Groups A, B, D) | 1–50 µg/ml |
| P. aeruginosa | 1–50 µg/ml |
| Eschericia coli | 1–50 µg/ml |
| Enterobacter spp. | 1–50 µg/ml |
| Klebsiella pneumoniae | 1–50 µg/ml |
| Streptococcus pneumoniae | 1–50 µg/ml |
| S. mutans | 1–50 µg/ml |
| Hemophilus influenze | 1–50 µg/ml |
| Proteus spp. | 1–50 µg/ml |
| Bacteroides gingivalis | 1–50 µg/ml |
| Streptococcus pyogenes | 1–50 µg/ml |
| Mycoplasma pneumoniae | 1–50 µg/ml |
| Respiratory Syncitial virus | 1–50 µg/ml |
| Influenza Virus | 1–50 µg/ml |
| Rhinovirus | 1–50 µg/ml |

An immunoglobulin composition of this invention which could be used universally in the treatment and prophylaxis of wounds, burns, nosocomial infections, oral and respiratory infections, and biomaterial or transplant material centered infections would have specific antibodies against each of the groups of potential pathogens of Table 17 within the concentration ranges. In particular applications, such as delayed release formulations, etc., the immunoglobulin compositions can be 20–100 times greater than those specified. Compositions containing lower or higher antibody titers to less or more than the above listed pathogens might also be used for the protection of certain infections. For instance a preparation containing high titer levels for S. aureus and P. aeruginosa may be acceptable in many clinical situations.

EXAMPLE 7

Biomaterial-centered, as well as wound and burn related infections in human and animal hosts may be prevented by using a full repertoire of immunoglobulins in-situ. This would be accomplished by directly applying an immunoglobulin composition containing a combination of IgG, IgA, and IgM to the wound, burn or biomaterial implant site, or to the surfaces of the biomaterial implant, to pre-opsonize microorganisms for rapid intracellular killing by host defense mechanisms. The application would occur prior to microbial attachment and biofilm formation, and preferably at the time of trauma, surgery, cleaning, debridement or within 4–6 hours thereafter. To decrease microbial adhesion and enhance endotoxin nuetralization, the IgA may be present at an elevated level compared to normal serum (e.g., 400–500 mg/dl) and the IgM may be present at an elevated level compared to normal serum (e.g., 200–300 mg/dl). Direct application of the full repertoire of immunoglobulins will produce an immunocompetent inflammatory zone sufficient to prevent adhesion of microorganisms to tissue and biomaterial surfaces.

While the invention has been described in terms of its preferred embodiments, those skilled in the art will recognize that the invention can be practiced with modification within the spirit and scope of the appended claims.

We claim:

1. A method for reducing infection associated with implantable and transplantable materials, comprising the steps of:

obtaining a material to be implanted or transplanted into a patient;

coating said material with an antibody composition selected from the group consisting of immunoglobulins, monoclonal antibodies, and mixtures thereof; and positioning said material in said patient.

2. The method of claim 1 wherein said obtaining step includes the step of selecting an organ or tissue of human or animal origin as said implantable or transplantable material, and wherein said step of positioning is performed by transplanting.

3. The method of claim 2 wherein said coating step is performed by a process selected from the group consisting of dipping and perfusing said organ or tissue.

4. The method of claim 1 wherein said obtaining step includes the step of selecting a biomaterial of non-animal origin as said implantable or transplantable material, and said positioning step is performed by implanting.

5. The method of claim 4 wherein said biomaterial is selected from the group consisting of catheters, total joints, fixation devices, pacemakers, central lines, contact lenses, artificial hearts, pumps, and drug delivery devices.

6. The method of claim 4 wherein said coating step is performed prior to said obtaining and positioning steps.

7. The method of claim 4 wherein said coating step is performed after said obtaining and before said positioning steps.

8. The method of claim 4 further comprising the step of immobilizing antibodies in said antibody composition on at least one surface of said material.

9. A method for enhancing the healing rate of damaged tissue, comprising the steps of:

applying an antibody composition to damaged tissue; and allowing said damaged tissue to heal, said antibody composition enhancing the rate of healing of said damaged tissue.

10. The method of claim 9 wherein said applying step includes the step of selecting said antibody composition to include immunoglobulins.

11. The method of claim 9 wherein said applying step includes the step of selecting said antibody composition to include monoclonal antibodies.

12. A body contacting device for preventing infection, comprising:

a biomaterial having at least one surface which will be brought into contact with a tissue or organ of a patient; and an antibody composition positioned on said surface of said biomaterial.

13. The body contacting device of claim 12 further comprising a matrix material positioned on said surface, said antibody composition being positioned within said matrix material on said surface of said biomaterial.

14. The body contacting device of claim 12 wherein said biomaterial is selected from the group consisting of catheters, total joints, fixation devices, pacemakers, central lines, contact lenses, vascular grafts, artificial hearts, pumps, diagnostic and monitoring devices, and devices including polymer packaged cells and therapeutics.

* * * * *